(12) United States Patent
Aerts et al.

(10) Patent No.: US 11,059,820 B2
(45) Date of Patent: Jul. 13, 2021

(54) CRYSTALLINE FORMS OF SELETALISIB

(71) Applicant: UCB BIOPHARMA SPRL, Brussels (BE)

(72) Inventors: Luc Lambert Jozef Jan Aerts, Brussels (BE); Georges Assaf, Brussels (BE); Nicolas Edmond Carly, Brussels (BE); Vincent Adolphe Carol Cool, Brussels (BE); Jean-Pierre Delatinne, Brussels (BE); Laurent Jacques Willy Delhaye, Brussels (BE); Jean Paul Kestemont, Brussels (BE); Sarah Le Meur, Brussels (BE)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 16/615,992

(22) PCT Filed: May 24, 2018

(86) PCT No.: PCT/EP2018/063640
§ 371 (c)(1),
(2) Date: Nov. 22, 2019

(87) PCT Pub. No.: WO2018/219772
PCT Pub. Date: Dec. 6, 2018

(65) Prior Publication Data
US 2020/0095246 A1    Mar. 26, 2020

(30) Foreign Application Priority Data
Jun. 2, 2017 (GB) ..................... 1708856

(51) Int. Cl.
  *C07D 471/04*  (2006.01)
  *A61K 31/519*  (2006.01)
  *A61P 3/00*    (2006.01)
  *A61P 9/00*    (2006.01)

(52) U.S. Cl.
  CPC ........ *C07D 471/04* (2013.01); *C07B 2200/13* (2013.01)

(58) Field of Classification Search
  CPC ....... C07D 471/04; A61K 31/519; A61P 3/00; A61P 9/00
  See application file for complete search history.

(56) References Cited

FOREIGN PATENT DOCUMENTS

WO    WO 2012/032334    3/2012

OTHER PUBLICATIONS

Caira Ed—Montchamp Jean-Luc: "Crystalline Polymorphism of Organic Compounds", Topics in Current Chemistry; Springer, Berlin, DE, vol. 198, Jan. 1, 1998, pp. 163-208.

*Primary Examiner* — Bruck Kifle
(74) *Attorney, Agent, or Firm* — McDonnell Boehnen Hulbert & Berghoff LLP

(57) ABSTRACT

Crystalline forms of seletalisib, designated as Form B and Form F and characterized herein, being selective inhibitors of PI3 kinase enzymes, in particular of the human PBKδ isoform, are accordingly of benefit in medicine, for example in the treatment of inflammatory, autoimmune, cardiovascular, neurodegenerative, metabolic, oncological, nociceptive or ophthalmic conditions.

13 Claims, 14 Drawing Sheets
(4 of 14 Drawing Sheet(s) Filed in Color)

CRYSTALLINE FORMS OF SELETALISIB

CROSS-REFERENCE TO RELATED APPLICATIONS

This application is a U.S. national phase of International Application No. PCT/EP2018/063640, filed May 24, 2018, which claims priority from Great Britain Application no. 1708856.8, filed Jun. 2, 2017, the disclosure of each of which is incorporated herein by reference in its entirety.

The present invention relates to crystalline forms of seletalisib, and to their use in therapy. More particularly, the present invention provides Form B and Form F of seletalisib.

The systematic chemical name of seletalisib is N-{(R)-1-[8-chloro-2-(1-oxypyridin-3-yl)quinolin-3-yl]-2,2,2-trifluoroethyl}pyrido[3,2-d]pyrimidin-4-ylamine. Seletalisib, which is specifically disclosed in WO 2012/032334, has the chemical structure represented by formula (I):

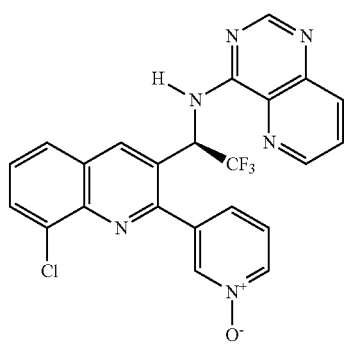

(I)

Seletalisib is a selective inhibitor of phosphoinositide 3-kinase (PI3K) enzymes, in particular of the human PI3Kδ isoform. Consequently, seletalisib is of benefit as a pharmaceutical agent, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

Being a potent and selective PI3K inhibitor, seletalisib is therefore beneficial in the treatment and/or prevention of various human ailments. These include autoimmune and inflammatory disorders such as Sjögren's syndrome, activated phosphoinositide 3-kinase delta syndrome (APDS), rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

Seletalisib is currently undergoing separate clinical trials to assess its suitability for the treatment of Sjögren's syndrome (including primary Sjögren's syndrome) and APDS.

As noted above, seletalisib is specifically disclosed in WO 2012/032334. However, there is no disclosure in that publication of specific crystalline forms of seletalisib.

WO 2016/170014 describes the use of seletalisib for the treatment of Sjögren's syndrome (including primary Sjögren's syndrome).

Copending international patent application PCT/EP2017/061567 (published on 23 Nov. 2017 as WO 2017/198590) describes the use of seletalisib for the treatment of activated phosphoinositide 3-kinase delta syndrome (APDS), also known as PASLI (p110δ-activating mutation causing senescent T cells, lymphadenopathy and immunodeficiency).

The crystal forms of the invention—i.e. Form B and Form F of seletalisib—possess advantageous properties, making them particularly amenable for formulation as pharmaceutical agents. In particular, the crystal forms of the invention demonstrate high thermodynamic physical stability (representing the ultimate equilibrium state) and/or high kinetic physical stability (representing the actual stability as a solid powder exposed to an environment of a specific temperature and relative humidity).

In a first aspect, the present invention provides Form B of seletalisib. Form B is a hydrated crystal form which can be prepared as described below. Form B can be represented by formula (IA):

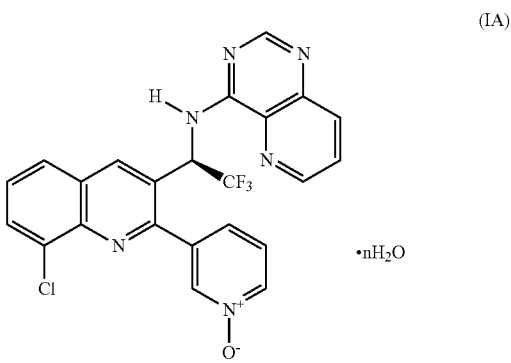 [SMILES: [O-][n+]1cccc(-c2nc3c(Cl)cccc3cc2[C@@H](Nc2ncnc3cccnc23)C(F)(F)F)c1]

(IA)

wherein n is at least about 0.1 and no more than about 2.1.

Suitably, n is at least about 0.9 and no more than about 2.1.

In a first embodiment, Form B exists as a monohydrate. Typically, n is at least about 0.9 and no more than about 1.5. Suitably, n is at least about 0.9 and no more than about 1.1. Generally, n is approximately 1.0.

In a second embodiment, Form B exists as a dihydrate. Typically, n is at least about 1.5 and no more than about 2.1. Suitably, n is at least about 1.9 and no more than about 2.1. Generally, n is approximately 2.0.

In a third embodiment, Form B exists as a variable water content hydrate wherein n is at least about 0.9 and no more than about 2.1. Suitably, n is at least about 1.0 and no more than about 2.0. Generally, n is approximately 1.5.

Analytical and characterization data for Form B of seletalisib are presented below.

In a second aspect, the present invention provides Form F of seletalisib. Form F is an anhydrous crystal form which can be prepared as described below.

Analytical and characterization data for Form F of seletalisib are presented below.

The present invention also provides a pharmaceutical composition which comprises Form B or Form F of seletalisib (hereinafter referred to as "the active ingredient") in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. sodium starch glycollate or croscarmellose sodium); or wetting agents (e.g. sodium lauryl sulphate). The tablets may be coated by methods well known in the art. Granules (e.g. for incorporation into capsules) may be obtained by methods well known from the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active ingredient.

For buccal administration, the compositions may take the form of tablets, lozenges or thin films formulated in conventional manner.

The active ingredient may be formulated for parenteral administration by injection, e.g. in the form of a microsuspension or nanosuspension for bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the active ingredient may also be formulated as a depot preparation. Such long-acting formulations may be administered by implantation or by intramuscular injection.

For nasal administration or administration by inhalation, the active ingredient may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the active ingredient may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the active ingredient may be formulated in a suitable lotion containing the active ingredient suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the active ingredient may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration the active ingredient may be formulated in an ointment such as petrolatum.

For rectal administration the active ingredient may be conveniently formulated as suppositories. These can be prepared by mixing the active ingredient with a suitable non-irritating excipient which is solid at room temperature but liquid at rectal temperature and so will melt in the rectum to release the active component. Such materials include, for example, cocoa butter, beeswax and polyethylene glycols.

The quantity of active ingredient required for the prophylaxis or treatment of a particular condition will vary depending on the active ingredient chosen, the medical indication, and the age and condition of the patient to be treated. In general, however, daily dosages from around 10 ng/kg to 1000 mg/kg body weight will typically be appropriate. The determination of dosage range and optimal dosage for a given patient is within the ordinary capability of the skilled practitioner.

Form F of seletalisib may be prepared by a process which comprises reacting the compound of formula (II) with a compound of formula (III):

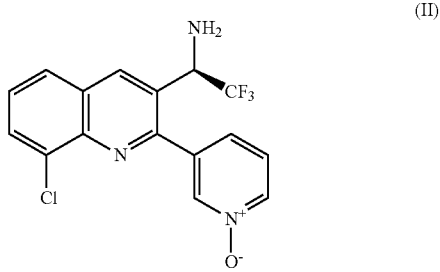

(II)

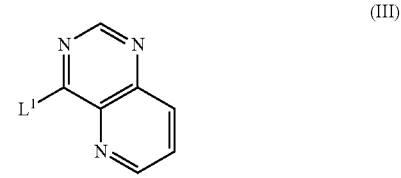

(III)

wherein $L^1$ represents $C_{1-6}$ alkoxy, optionally substituted aryloxy, optionally substituted arylthio or optionally substituted heteroaryl; under anhydrous conditions.

In a first embodiment, $L^1$ represents $C_{1-6}$ alkoxy, especially $C_{1-4}$ alkoxy. In a second embodiment, $L^1$ represents unsubstituted aryloxy or substituted aryloxy. In a third embodiment, $L^1$ represents unsubstituted arylthio or substituted arylthio. In a fourth embodiment, $L^1$ represents unsubstituted heteroaryl or substituted heteroaryl.

The term "alkyl" as used herein includes straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy" are to be construed accordingly.

Where $L^1$ represents $C_{1-6}$ alkoxy, suitable values include methoxy, ethoxy, n-propoxy, n-butoxy and isobutoxy. A particular value of $L^1$ is ethoxy.

Typical examples of optional substituents on $L^1$ include one to five (preferably one, two or three) substituents independently selected from halogen, nitro, $C_{1-6}$ alkyl, $C_{1-6}$ alkoxy and di($C_{1-6}$)alkylamino.

Typical examples of specific substituents on $L^1$ include one to five (preferably one, two or three) substituents independently selected from fluoro, chloro, nitro, methyl, methoxy and dimethylamino.

The term "aryl" as used herein refers to monovalent carbocyclic aromatic groups derived from a single aromatic ring or multiple condensed aromatic rings. Suitable aryl groups include phenyl and naphthyl, preferably phenyl. Derived expressions such as "aryloxy" and "arylthio" are to be construed accordingly.

Where $L^1$ represents optionally substituted aryloxy, typical values include unsubstituted phenoxy and substituted phenoxy. Suitable values include phenoxy, pentafluorophenoxy, chlorophenoxy (especially 4-chlorophenoxy), nitrophenoxy (especially 4-nitrophenoxy), methylphenoxy (especially 4-methylphenoxy), trimethylphenoxy (especially 2,4,6-trimethylphenoxy) and methoxyphenoxy (especially 4-methoxyphenoxy).

Where $L^1$ represents optionally substituted arylthio, typical values include unsubstituted phenylthio and substituted phenylthio. Suitable values include phenylthio.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include imidazolyl, triazolyl and pyridinyl.

Where $L^1$ represents heteroaryl, typical values include unsubstituted heteroaryl and substituted heteroaryl. Suitable values include imidazolyl (especially imidazol-1-yl), triazolyl (especially 1,2,4-triazol-1-yl) and dimethylaminopyridinium (especially 4-(dimethylamino)pyridinium-1-yl).

Suitable values of $L^1$ include methoxy, ethoxy, n-propoxy, n-butoxy, isobutoxy, phenoxy, pentafluorophenoxy, 4-chlorophenoxy, 4-nitrophenoxy, 4-methylphenoxy, 2,4,6-trimethylphenoxy, 4-methoxyphenoxy, phenylthio, imidazol-1-yl, 1,2,4-triazol-1-yl and 4-(dimethylamino)pyridinium-1-yl.

The reaction between compounds (II) and (III) is generally performed in the presence of an acid, e.g. a mineral acid such as hydrochloric acid. The reaction may be conveniently effected at an elevated temperature in an anhydrous solvent, e.g. a $C_{1-4}$ alkanol such as anhydrous n-propanol.

The intermediate of formula (II) may be prepared by the method described in the accompanying Examples; or by a procedure analogous to any one of those described in WO 2012/032334.

The intermediates of formula (III) may be prepared by the method described in the accompanying Examples, or by procedures analogous thereto.

Form B of seletalisib may be prepared by a process which comprises contacting Form F of seletalisib with water in an organic solvent (e.g. as a solution or slurry); followed by crystallization therefrom.

Appositely, Form F of seletalisib may be dissolved in a mixture of water and a cyclic ether solvent, e.g. 2-methyltetrahydrofuran, at an elevated temperature, e.g. a temperature in the region of 40° C. Typically, the mixture may be treated with a base, e.g. an alkali metal hydroxide such as sodium hydroxide, to attain a pH in the region of 10.5. After washing the organic phase with aqueous medium, e.g. water and/or brine, to re-establish neutral pH, the mixture may typically be redissolved in an alternative solvent, e.g. a $C_{1-4}$ alkanol such as 2-propanol, then treated with water and heated at a temperature in excess of 65° C. After slow cooling to a temperature in the region of 20° C., more water is slowly added. The mixture is then gradually cooled and aged, generally at a temperature in the region of 0° C., before the product is allowed to crystallize from the mixture and collected.

Form B of seletalisib may be converted into Form F by a process which comprises contacting Form B of seletalisib with a water-free medium (e.g. as a solution or slurry); followed by crystallization therefrom.

Appositely, Form B of seletalisib may be dissolved in a substantially water-free solvent, e.g. a $C_{1-4}$ alkanol such as 2-propanol, at an elevated temperature, e.g. a temperature in the region of 50° C.; followed by partial distillation of the solvent and slow cooling to a temperature in the region of 0° C.; before the product is allowed to crystallize from the reaction mixture and collected.

The following Examples illustrate the preparation, analysis and characterization of Form B and Form F of seletalisib.

PREPARATIVE EXAMPLES

Intermediate 1

2,8-Dichloroquinoline-3-carbaldehyde

A reactor was charged with 2-methyltetrahydrofuran (50 mL). The reactor was cooled to −10° C., then n-butyllithium (24 mL of a 2.5M solution in hexane) was charged dropwise into the reactor. The mixture was stirred for 10 minutes, then a solution of 2,2,6,6-tetramethylpiperidine (8.9 g) in 2-methyltetrahydrofuran (7.5 mL) was slowly added. The mixture was stirred for 10 minutes at −10° C., then warmed to 0° C. After 1 h at 0° C., the reactor was cooled to −78° C. A separately prepared solution of 2,8-dichloroquinoline (7.5 g) in 2-methyltetrahydrofuran (50 mL) was charged dropwise into the reactor whilst maintaining the reaction temperature below −70° C. The reactor was charged dropwise with 4-formylmorpholine (7.2 g) whilst maintaining the reaction temperature below −70° C. Aqueous citric acid solution (25 wt %; 3.5 mL) was added dropwise at −78° C. The reaction mixture was allowed to warm slowly to room temperature. An aqueous solution of citric acid (25 wt %; 30 mL) was added at room temperature, then the mixture was heated to 45-50° C. and stirred for 1 h. The organic phase was separated, then washed with 10% citric acid (30 mL) and water (30 mL). The washed organic layer was concentrated under vacuum until approximately 5.5 vol, then maintained at ~60° C. until crystallization commenced. The mixture was aged, then cooled to 0° C. with the slow addition of heptanes (60 mL). The residue was aged at 0° C., then filtered and washed with heptanes (30 mL). The wet material was dried at 40° C. under vacuum, to afford the title compound.

Notes

The reaction as described above is performed in 2-methyltetrahydrofuran. An alternative solvent that can be employed in the above reaction is tetrahydrofuran. It is believed that diethyl ether, tert-butyl methyl ether and/or cyclopentyl methyl ether could also be employed as alternative solvents.

The reaction as described above employs the lithium salt of 2,2,6,6-tetramethylpiperidine. An alternative reagent that can be employed is the lithium salt of diisopropylamine.

Intermediate 2

8-Chloro-2-(pyridin-3-yl)quinoline-3-carbaldehyde

A nitrogen-flushed reactor was charged with Intermediate 1 (10 g), tris-(dibenzylideneacetone)dipalladium(0) (200 mg), tri-tert-butylphosphonium tetrafluoroborate (200 mg), 3-pyridinylboronic acid (6 g), degassed ethanol (120 mL), degassed water (30 mL) and triethylamine (7.7 mL). The mixture was heated at 70° C. until the reaction was complete, then the temperature was decreased to 20° C. and the mixture was filtered. The reactor and the filter cake were washed with water (2×5 volumes). The wet cake was suspended in a mixture of water (5 volumes) and acetonitrile (5 volumes). The slurry was heated to 60-65° C., then hydrochloric acid (33%; 1.3 equiv) was added, followed by triethylamine (1.4 equiv). The mixture was aged for 1 h, then cooled to 20° C. and filtered. The wet cake was washed with water/ethanol (50:50 mixture). The cake was dried under vacuum at 40° C., to afford the title compound.

Intermediate 3

(NE)-N-{[8-Chloro-2-(pyridin-3-yl)quinolin-3-yl]methylene}-2-methylpropane-2-sulfinamide To a nitrogen-purged reactor were charged (S)-(−)-2-methyl-2-propanesulfinamide (27 g), $K_2HPO_4$ (5.4 g) Intermediate 2 (50 g) and $K_3PO_4$ (31.5 g), followed by tetrahydrofuran (165 mL). The suspension was heated at 40-45° C. until the reaction was complete, then the mixture was cooled to 10° C. $KH_2PO_4$ (22.7 g) and water (13 volumes) were added, and the slurry was stirred at 20° C., then filtered. The solid residue was washed with water and with an aqueous solution of $KH_2PO_4$, then dried under vacuum at 40° C., to afford the title compound.

Intermediate 4

N-{(1R)-1-[8-Chloro-2-(pyridin-3-yl)quinolin-3-yl]-2,2,2-trifluoroethyl}acetamide, Methanol Solvate A nitrogen-purged reactor was charged with Intermediate 3 (20 g), tetrabutylammonium acetate (3.24 g) and toluene (140 mL). The mixture was cooled to 0° C. and (trifluoromethyl)trimethylsilane (11.5 g) was added, maintaining the reaction temperature at 0-5° C. The reaction mixture was stirred at 0-5° C. until the reaction was complete. The mixture was warmed to 20° C., then poured onto water (100 mL). The aqueous phase was discarded and the organic layer was washed again with water. The resulting toluene solution was treated with water (20 mL) and concentrated aqueous HCl (5.25 equiv). The reaction mixture was heated at 50° C. After the reaction was complete, the aqueous layer was extracted with fresh toluene (60 mL), at 50-70° C., then a neutralizing amount of 30% aqueous NaOH solution was added. The organic layer was separated and the aqueous layer was re-extracted at 70° C. with toluene (3 volumes). The combined organic phases were washed at 70° C. with water (3 volumes), then concentrated to a dilution of approximately 2.5 volumes. The residue was cooled to 5-10° C., then triethylamine (1.5 equiv) was added. Acetic anhydride (1.3 equiv) was added dropwise, maintaining the reaction temperature below 10° C. The reaction mixture was heated at 40-45° C. for 1 h, then methanol (~1.1 volume) was added. Crystallization was observed, then the suspension was cooled to −10° C. and filtered. The cake was washed with methanol at −10° C. The resulting solid was dried under vacuum at 40° C. to afford the title compound.

Intermediate 5

N-{(1R)-1-[8-Chloro-2-(1-oxidopyridin-1-ium-3-yl)quinolin-3-yl]-2,2,2-trifluoroethyl}-acetamide Intermediate 4 was introduced into a reactor. Acetonitrile (5 volumes) was transferred into the reactor, then acetic acid (1.42 equiv) and 1.5M aqueous $KHCO_3$ solution (5 volumes) were added. The mixture was heated to 40° C., then peracetic acid (39% w/w solution in acetic acid, 2.0 equiv) was added dropwise. The mixture was stirred at 40° C. until the reaction was complete. A 1M aqueous solution of $Na_2S_2O_3$ (3.0 volumes) was added dropwise at 40° C. The mixture was cooled to 25° C., then a 1M aqueous NaOH solution (~7 volumes) was added until pH 7-13, followed by water (5.0 volumes). The slurry was cooled to 0° C., then filtered. The wet filter cake was washed with water. The resulting wet solid was dried under vacuum at 40° C. to afford the title compound.

Intermediate 6

Pyrido[3,2-d]pyrimidin-4-ol

A reactor was charged with isobutanol (50 g) and formamidine acetate (45 g). The slurry was heated to 75-85° C., then 3-aminopicolinic acid (25 g) was added portionwise. The slurry was heated under reflux until reaction was complete. The reaction mixture was cooled to 20° C., then water (3.1 mL) was added. The slurry was stirred for 1 h and filtered, then washed with water and dried under vacuum at 40° C., to afford the title compound.

Intermediate 7

4-Ethoxypyrido[3,2-d]pyrimidine

To a suspension of Intermediate 6 (10 g) in ethyl acetate (50 mL) was added N,N-dimethylethylamine (13.8 g). The mixture was cooled to 0-5° C., then trifluoroacetic anhydride (15.8 g) was added. After completion of the reaction, a 2.7 M solution of sodium ethoxide in ethanol (59 mL) was added slowly. After completion of the reaction, acetic acid (1.94 mL) was added, and the remaining N,N-dimethylethylamine and ethanol were removed by distillation. A 20% aqueous KCl solution (5 volumes) was added, then the phases were separated at 50° C. The aqueous layer was re-extracted with ethyl acetate (2×3 volumes) at 50° C. The combined organic layers were azeodried, then solvent-switched to methylcyclohexane. The concentration was adjusted to 7-8 volumes. The distillation residue was washed at 90° C. with 20% aqueous KCl solution (0.5 volumes). The organic layers were slowly cooled to 0° C. The resulting solid was filtered and washed with methylcyclohexane, then dried under vacuum at 40° C., to afford the title compound.

Example 1

N-{(R)-1-[8-Chloro-2-(1-oxypyridin-3-yl)quinolin-3-yl]-2,2,2-trifluoroethyl}pyrido[3,2-d]pyrimidin-4-ylamine, Crystal Form F A solution of concentrated sulfuric acid (1.25 volumes) in water (total volume of solution ~4 volumes) was prepared in a reactor, then Intermediate 5 was added at room temperature. The resulting solution was heated at 70° C. and maintained at that temperature until the reaction was complete. The reaction mixture was cooled to 0° C., then 2-methyltetrahydrofuran (1.0 volume) was added and the reaction mixture was neutralized by the addition of 28% ammonia. After phase separation, the aqueous layer was extracted with 2-methyltetrahydrofuran. The combined organic layers were washed with water, then the resulting solution was filtered on charcoal. The solvent was switched to n-propanol, then azeodried. To the distillation residue (~3 volumes) was charged Intermediate 7 (1.1 equiv), then the internal temperature was increased to 60° C. To the reaction mixture at 60° C. was added 1M HCl solution (0.09 equiv) (prepared by adding acetyl chloride to n-propanol in a separate vessel). The resulting mixture was stirred and maintained at 60° C. until the reaction was complete. The mixture was cooled slowly to −5° C., then the residue was collected by filtration. The wet cake was washed with n-propanol, pre-cooled to −5° C. The residue was dried in a vacuum oven at 40° C., to afford the title compound.

Example 2

N-{(R)-1-[8-Chloro-2-(1-oxypyridin-3-yl)quinolin-3-yl]-2,2,2-trifluoroethyl}pyrido[3,2-d]pyrimidin-4-ylamine, Crystal Form B (Hydrate)

Example 1 was dissolved in 2-methyltetrahydrofuran/water (26 volumes:4.5 volumes), at 40° C., by addition of NaOH until pH 10.5±0.5. The aqueous layer was discarded. The organic layer was washed with brine, then with water, until the pH of the aqueous layer was neutral. The solvent was switched to 2-propanol by distillation under vacuum (if required, 2-propanol can be added until dissolution at 65-75° C.). Water was added slowly to the solution at >65° C., until the 2-propanol:water ratio was approximately 80:20. The mixture was cooled slowly to 20° C., then water was added slowly until the 2-propanol:water ratio was approximately 40:60. The mixture was aged for 0.5 h, then cooled slowly to 0° C. The slurry was aged overnight. The residue was collected by filtration, then washed with 2-isopropanol/water (40:60) at 0° C., to afford the title compound.

Example 3

Conversion of Crystal Form B (Hydrate) to Crystal Form F

Example 2 was dispersed in 2-propanol (7 volumes). After aging at 50° C. for 1 h, the solvent (1.0-1.5 volumes) was removed by distillation. The mixture was cooled slowly to 0° C., then filtered. The wet cake was dried under vacuum at 40° C.

Analytical Examples

X-Ray Powder Diffraction (XRPD)

XRPD patterns were collected on a Bruker D8 diffractometer using Cu Kα radiation (40 kV, 40 mA), θ-2θ goniometer, divergence of V12 and a Lynxeye detector. The software used for data collection was Diffrac Plus XRD Commander 2.6.1 and the data were analysed using Diffrac Plus Eva 13.0.0.3.

Samples were put on single crystal supports, which were rotated in their own plane during the analysis with the following data collection settings:
Angular range 4.5 to 30° 2θ.
Increment: 0.02.
Time per step: 0.5 s/step.

Crystal Packing

Crystal diffraction measurements of the solid forms were collected on a single crystal X-ray diffractometer, model Oxford Gemini R Ultra, Mo anode. Crystal structure was resolved therefrom using the method SHELXL-97.

Differential Scanning Calorimetry (DSC)

DSC thermograms were obtained using a TA Instruments Q2000 calorimeter. The calibration for thermal capacity was carried out using Sapphire and the calibration for temperature and energy was carried out using Certified Indium. Either aluminium pierced pan of 40 μL or closed stainless steel pan of 100 μL were heated at 10° C./minute from 25° C. to 300° C. A purge of dry nitrogen at 50 mL/minute was maintained over the sample. Data were collected with Thermal Advantage (Q series) version 5.4.0 and analyzed with Universal Analysis version 4.5A.

Thermo-Gravimetric Analysis (TGA)

TGA thermograms were collected on a Mettler Toledo TGA/SDTA851e. A 100 μL aluminium pan was heated at 10° C./minute from 25° C. to 500° C. A nitrogen purge at 50 mL/minute was maintained on the thermobalance and the oven during the measurement. Data were collected and analyzed with Stare software, version 9.30.

Dynamic Vapor Sorption (DVS)

Two different types of DVS equipment were used, where the sample weight uptake is plotted against the relative humidity over the sample:
SMS DVS controlled by the software DVS Win. The sample temperature is maintained at 25° C. The weight change of the sample as a function of % RH (relative humidity expressed as a percentage) was monitored by the microbalance. The sample was placed on a glass pan attached to the microbalance. A moisture cycle was performed from 30 to 90 to 0 to 30% RH at 25° C. (dm/dt 0.002 with a scanning step 10%).
Projekt Messtechnik Sorptions Prüfsystem SPS 11-100n or Surface Measurement Systems DVS-1; the sample was placed on an aluminium (SPS 11) or platinum (DVS-1) holder on top of the microbalance and conditioned at 25% RH and 25° C. A moisture cycle was performed from 25 to 95 to 0 to 25% RH at 5% RH per hour at 25° C.

The patent or application file contains at least one drawing executed in color. Copies of this patent or patent application publication with color drawings will be provided by the Office upon request and payment of the necessary fee.

Form B

FIGS. 1 to 3 illustrate the XRPD patterns of the hydrated solid form having different hydration ratios: hydrate.nH$_2$O with 0<n≤2. FIG. 1: n=2. FIG. 2: n=1. FIG. 3: n≤1. The XRPD patterns exhibit variable characteristic peaks at: 11.0° to 11.1°, 12.5° to 12.6°, 20.9° to 21.1°, and 22.9° to 23.0° 2θ±0.2° 2θ.

FIG. 4 shows the DSC thermogram of the hydrate.nH$_2$O performed in closed pan. The hydrated solid form exhibits an endothermic event at 146° C.±6° C. followed by an exothermic event corresponding to a recrystallization into the anhydrous Form F and subsequent melting of Form F.

FIG. 5 shows the TGA thermogram of the hydrate.nH$_2$O. Two distinct weight losses as well as a continuous slope at the beginning of the spectrum were observed. The continuous slope represents the water at the surface of the crystals, whilst the weight loss (5.97% corresponding to 1.7 molecules) identified between 25° C. and 150° C. corresponds to the release of the water associated with the crystal packing. The second important weight loss observed, starting from ~210° C., corresponds to the degradation of the product.

FIG. 6 depicts the DVS curve, showing the water sorption and desorption of the hydrate under variable relative humidity. From 25% RH to 95% RH a continuous water uptake is observed (~2.4% weight). In the second part of the cycle (95% RH to 0% RH), the sample loses mass continuously and a stepwise mass loss of 3.3% weight is observed at low RH. In the third part (0% RH to 25% RH), the sample shows a stepwise water uptake of 3.6%. The DVS profile clearly shows the variable water content behaviour of the hydrate.nH$_2$O. The sample was checked by XRPD pre- and post-measurement and a slight shift of diffraction peaks was observed.

|  |  | Hydrate•1H$_2$O orthorhombic P2$_1$2$_1$2$_1$ | Hydrate•2H$_2$O orthorhombic P2$_1$2$_1$2$_1$ |
|---|---|---|---|
|  | Space group |  |  |
| Unit Cell Dimension | Cell lengths [Å] | a 9.169(2) B 14.9626(14) C 16.545(5) | a 9.0686(3) b 14.8654(5) C 16.9944(6) |
|  | Cell Angles | A 90.00 B 90.00 γ 90.00 | A 90.00 B 90.00 γ 90.00 |
|  | Cell Volume | 2269.84 Z: 4 Z': 0 | 2290.99 Z: 4 Z': 0 |

FIGS. 7 and 8 illustrate the crystal packing of the hydrate.nH$_2$O with n=2 and n=1 respectively.

FIG. 9 provides a structural overlay of the hydrate.nH$_2$O with n=1 and n=2, showing the perfect superimposition of both crystal packings, the only difference being the number of incorporated water molecules.

Thermodynamic and Kinetic Stability of Form B

The hydrated solid form (Form B) was found to be thermodynamically stable under ICH conditions, meaning 25° C./60% RH and 40° C./75% RH. The thermodynamic stability was checked by suspending crystals of Form B for 30 days in appropriate solvent/water mixtures, thus creating environments with the desired water activity. As water activity is equivalent to relative humidity (e.g. 60% RH=water activity 0.6), and due to the more rapid exchange of molecules between the crystals and the saturated solution in the suspension, this approach gives the possibility to observe the equilibrium condition of the solid form. Accordingly, Form B was also found to be kinetically stable for 7 weeks at 25° C./60% RH and at 40° C./75% RH. Kinetic stability was checked by exposing solid, powdery samples to air at selected temperature and relative humidity.

Form F

FIG. 10 illustrates the XRPD pattern of the anhydrous form. Characteristic peaks of the anhydrous form are observed at 6.4°, 8.7°, 15.2°, 15.5°, and 20.3° 2θ±0.2° 2θ.

FIG. 11 shows the DSC thermogram of the anhydrous form. This solid form exhibits a characteristic melting endotherm at 238.5° C.±5° C., followed by an exotherm. This suggests that the sample decomposes upon melting.

Table 2 provides the crystal lattice data for the anhydrous form.

|  |  | Anhydrous form orthorhombic P2$_1$2$_1$2$_1$ |
|---|---|---|
|  | Space group |  |
| Unit Cell Dimension | Cell lengths [Å] | a 11.4304(4) B 18.3469(7) C 20.3019(11) |
|  | Cell Angles | A 90.00 B 90.00 γ 90.00 |
|  | Cell Volume | 4257.56 Z: 8 Z': 0 |

Figure 1:
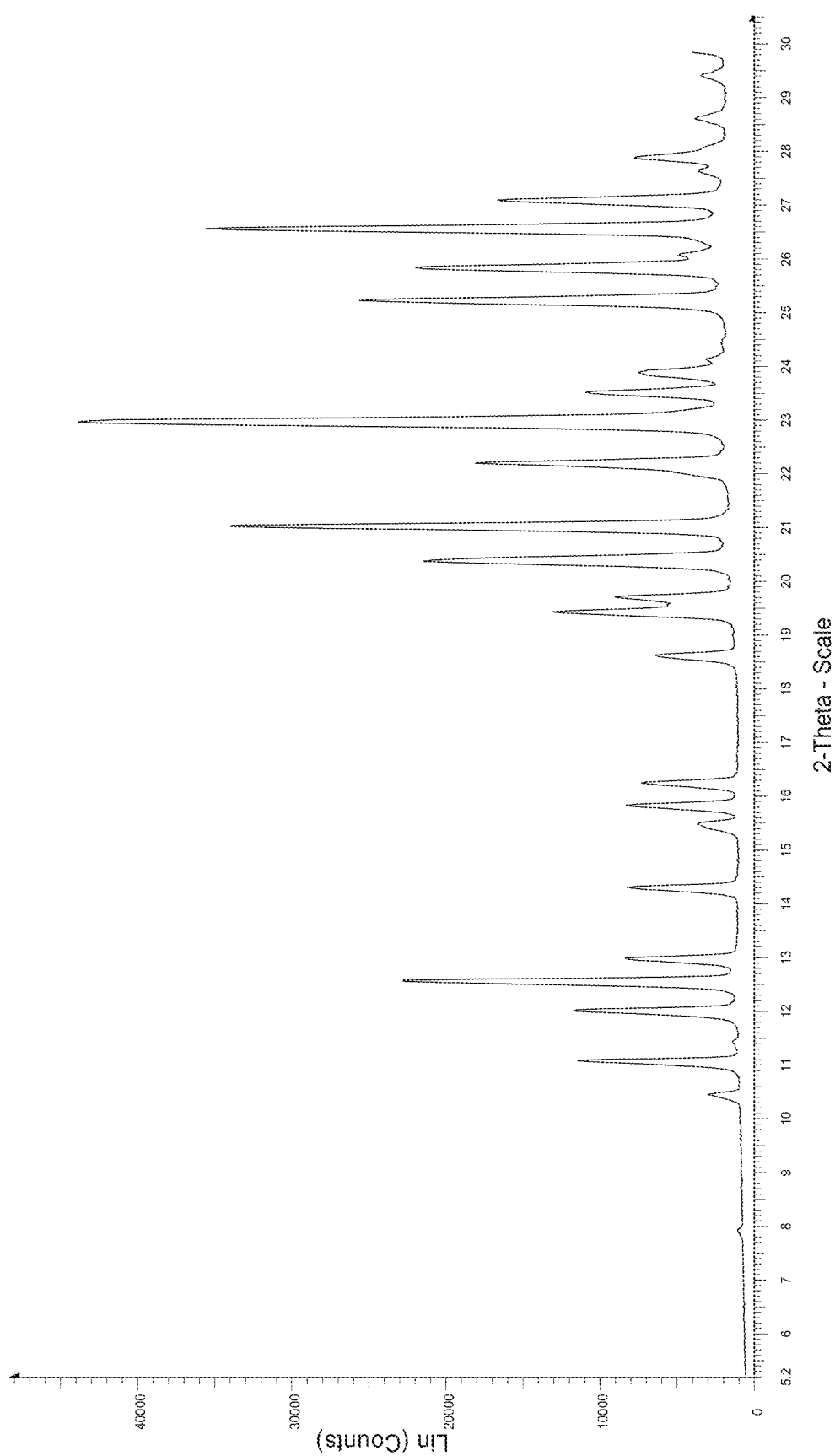
Figure 2:
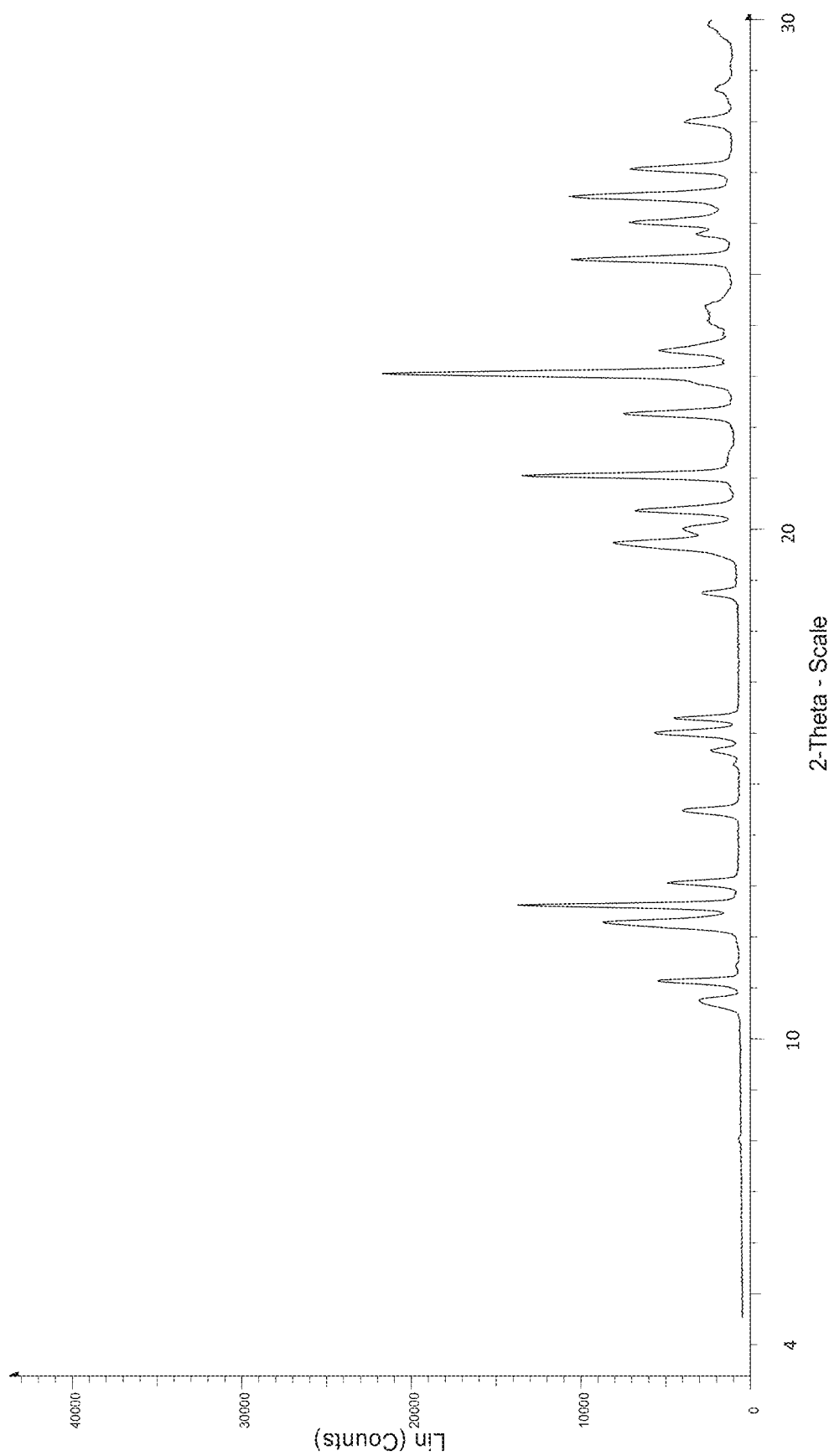
Figure 3:
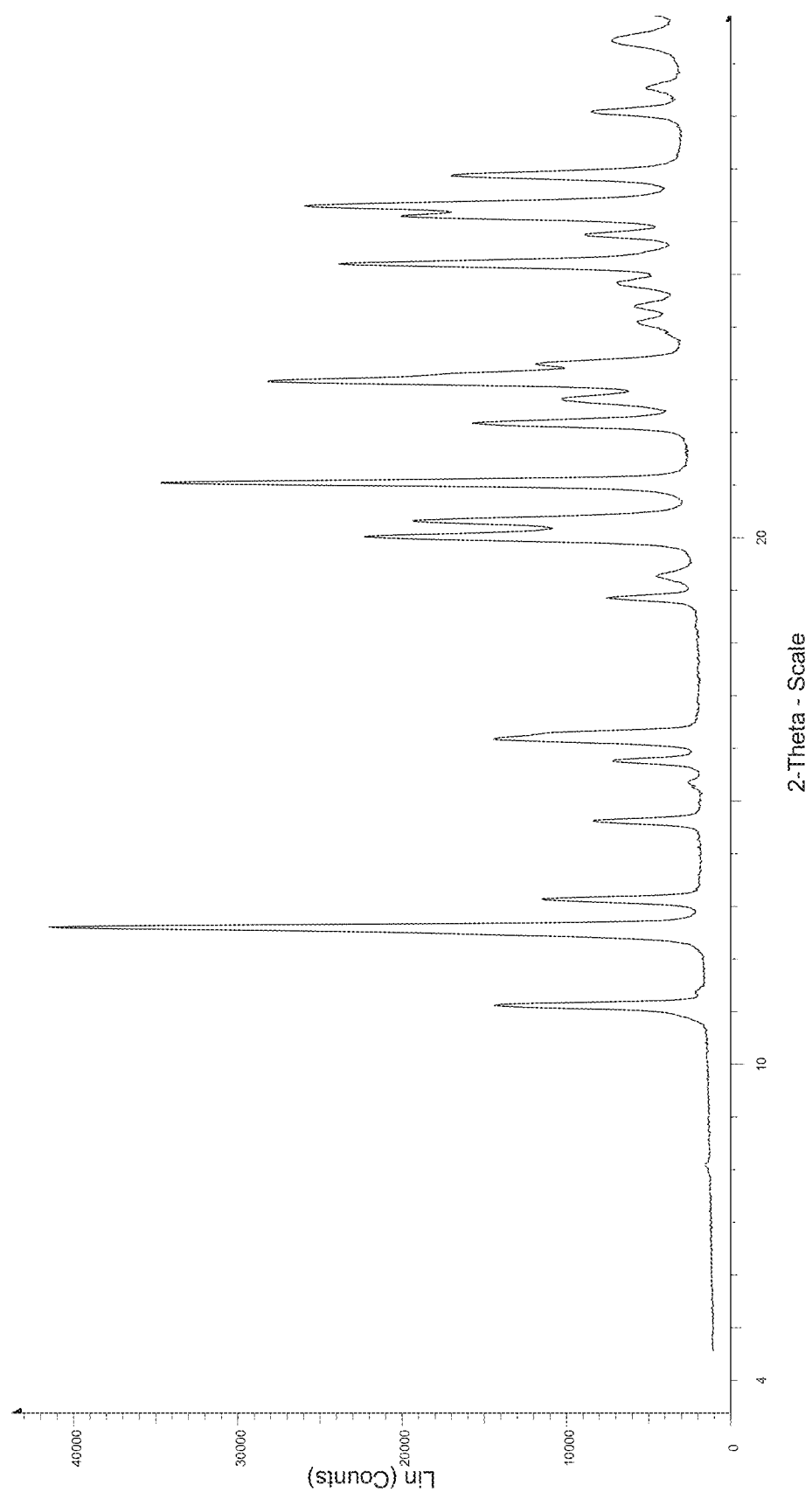
Figure 4:
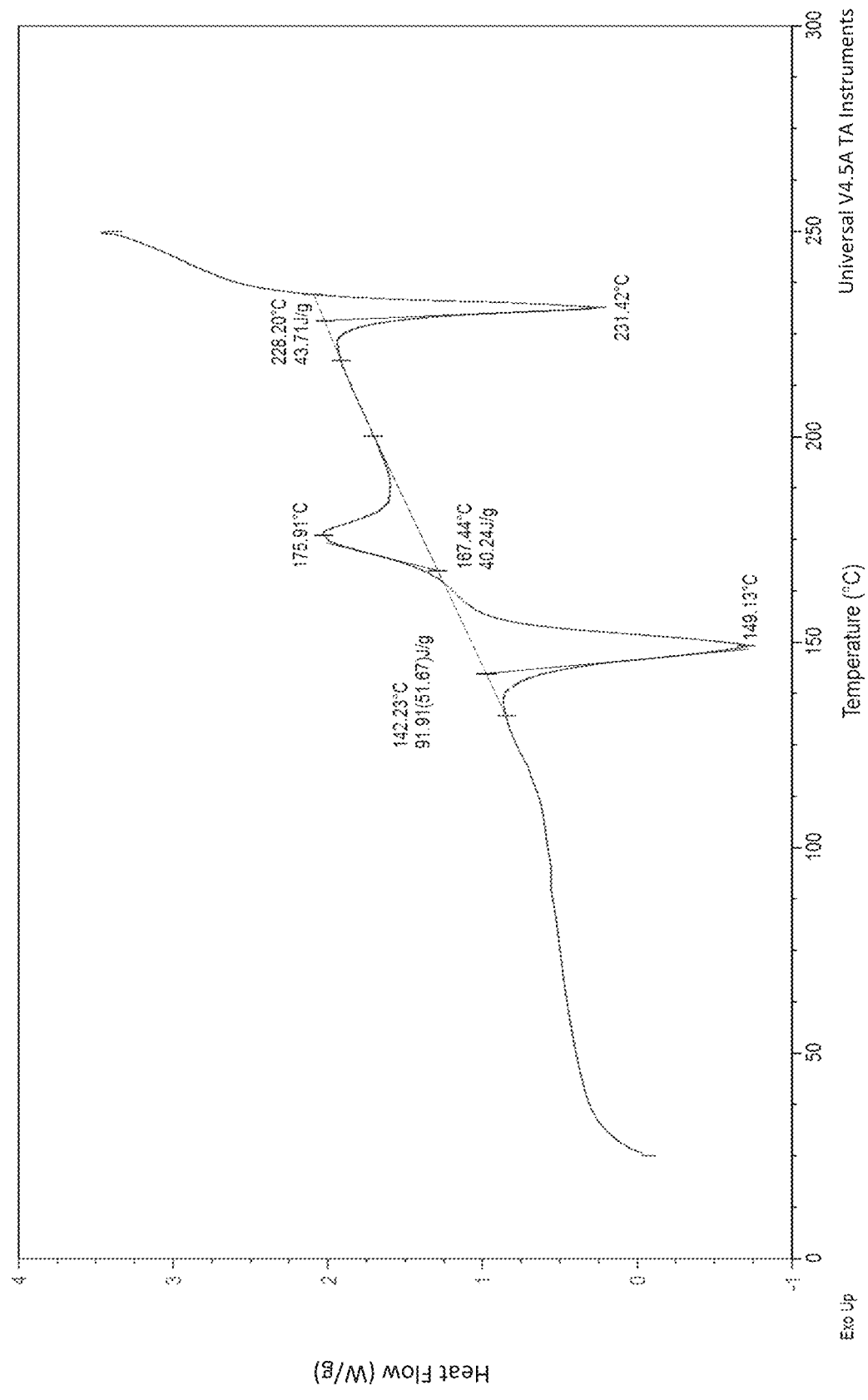
Figure 5:
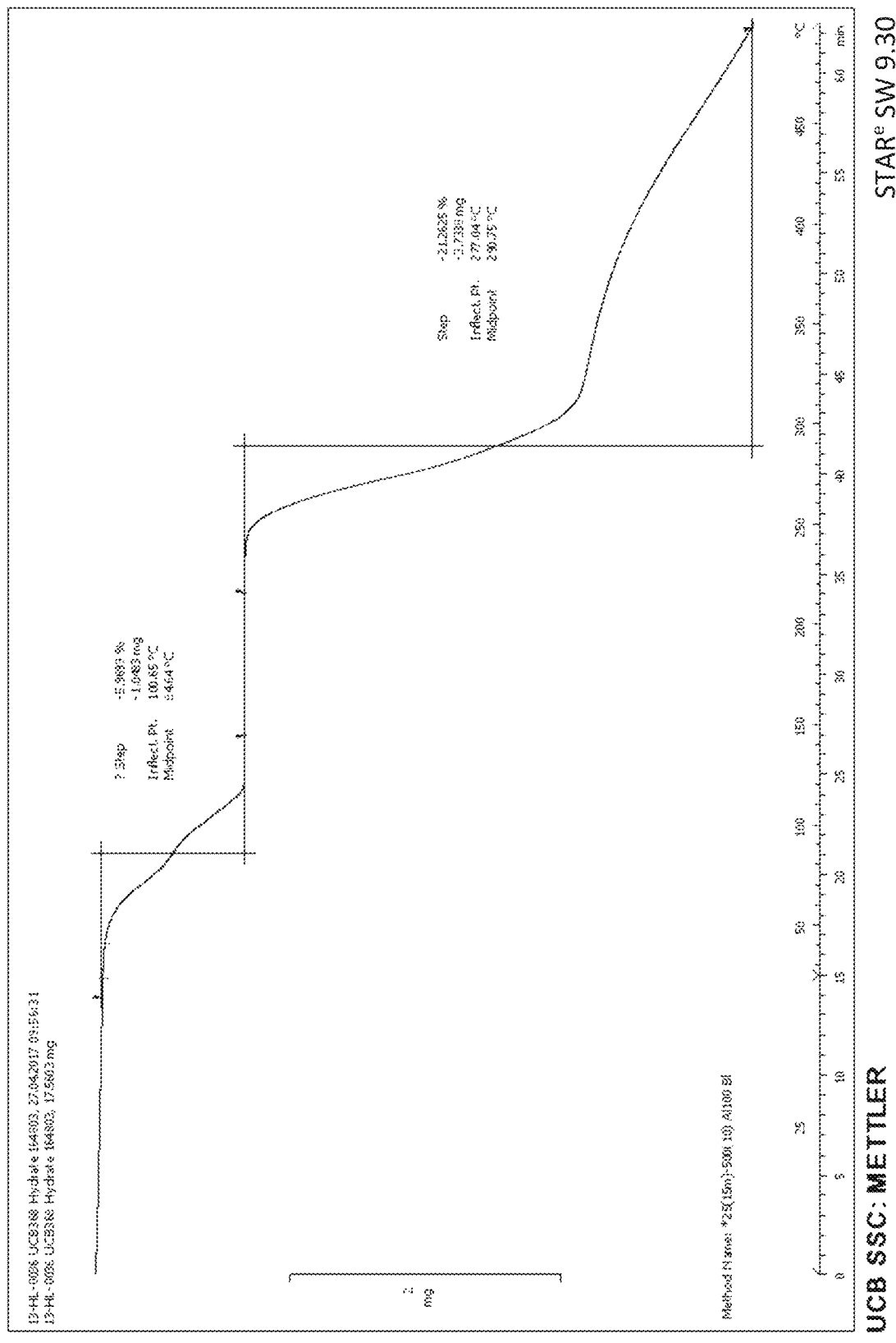
Figure 6:
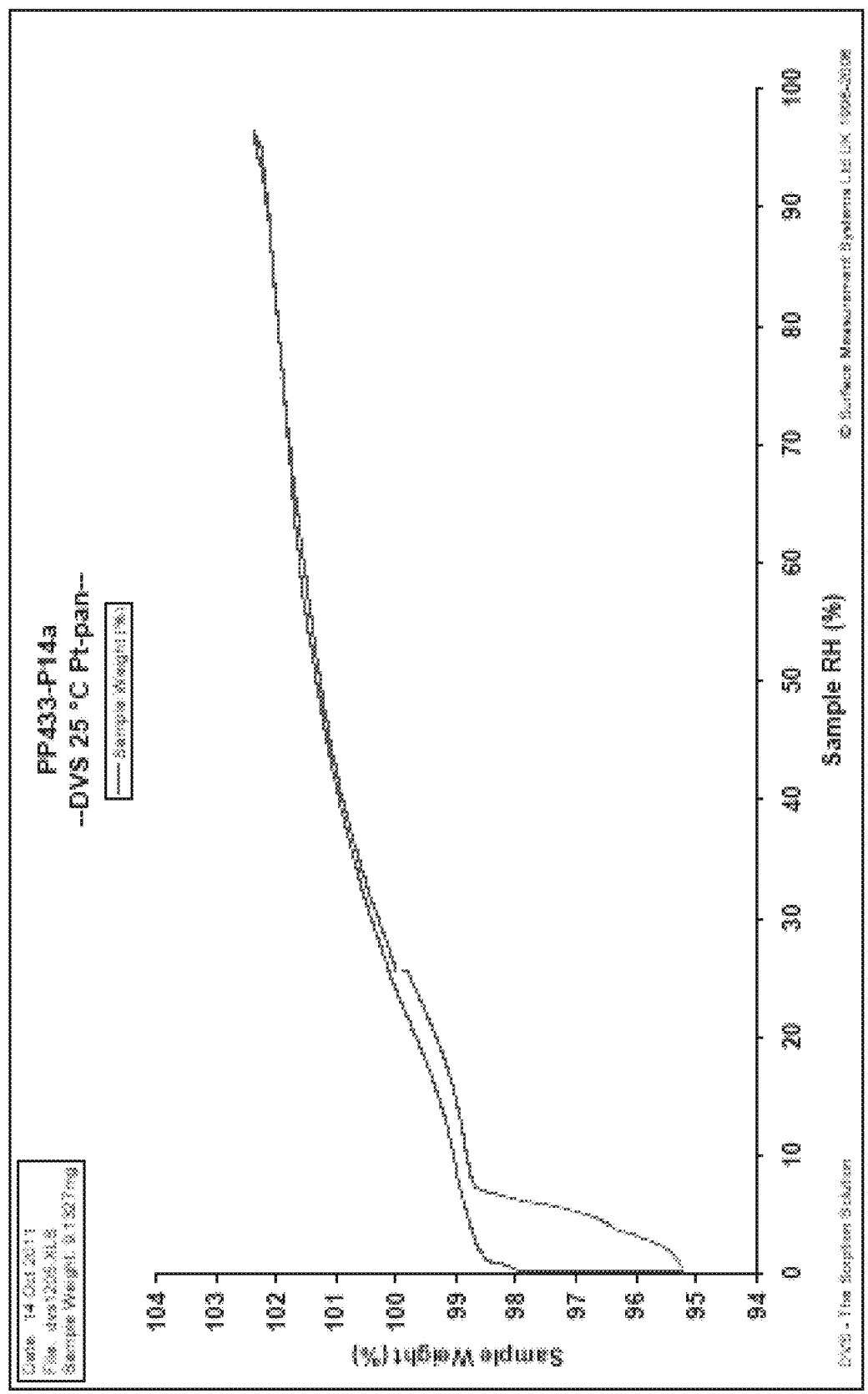
Figure 7:
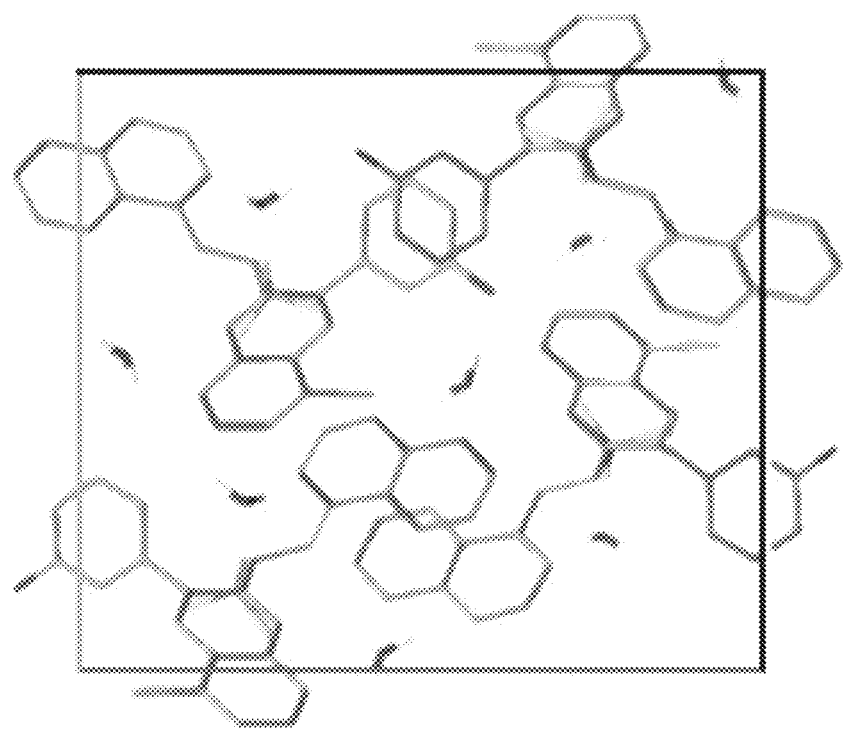
Figure 8:
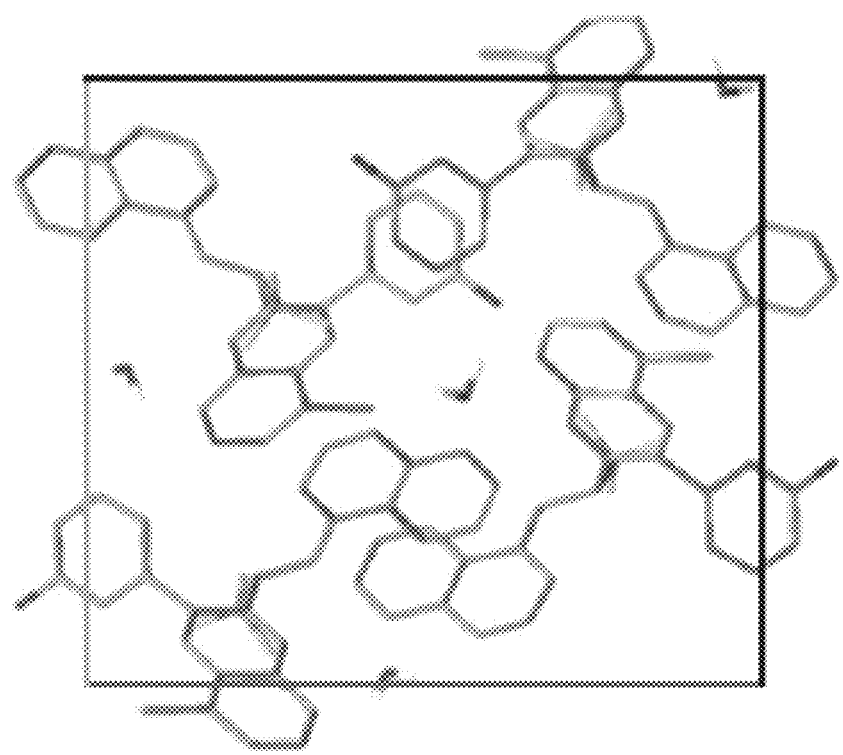
Figure 9:
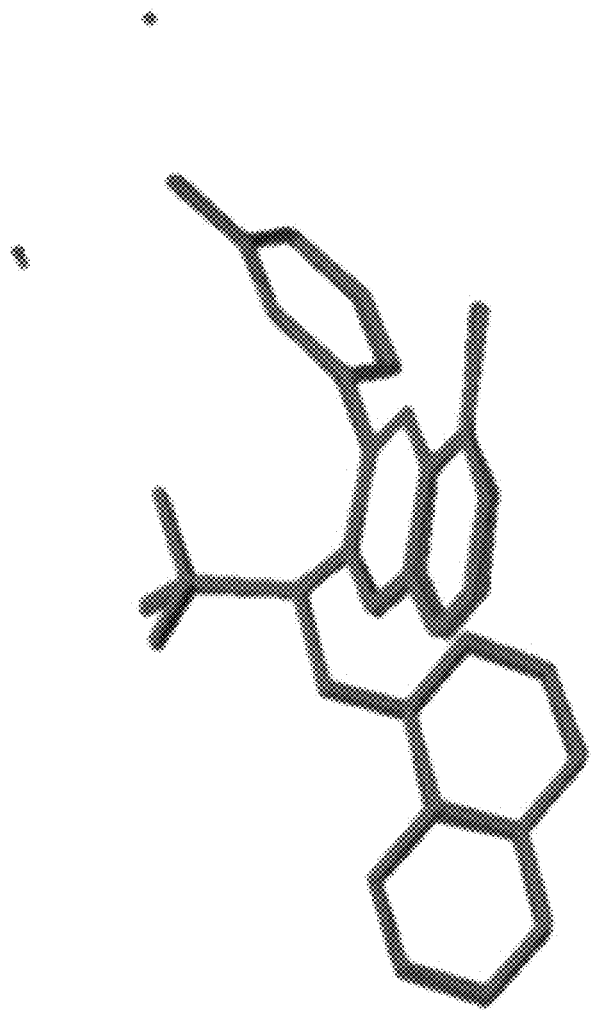
Figure 10:
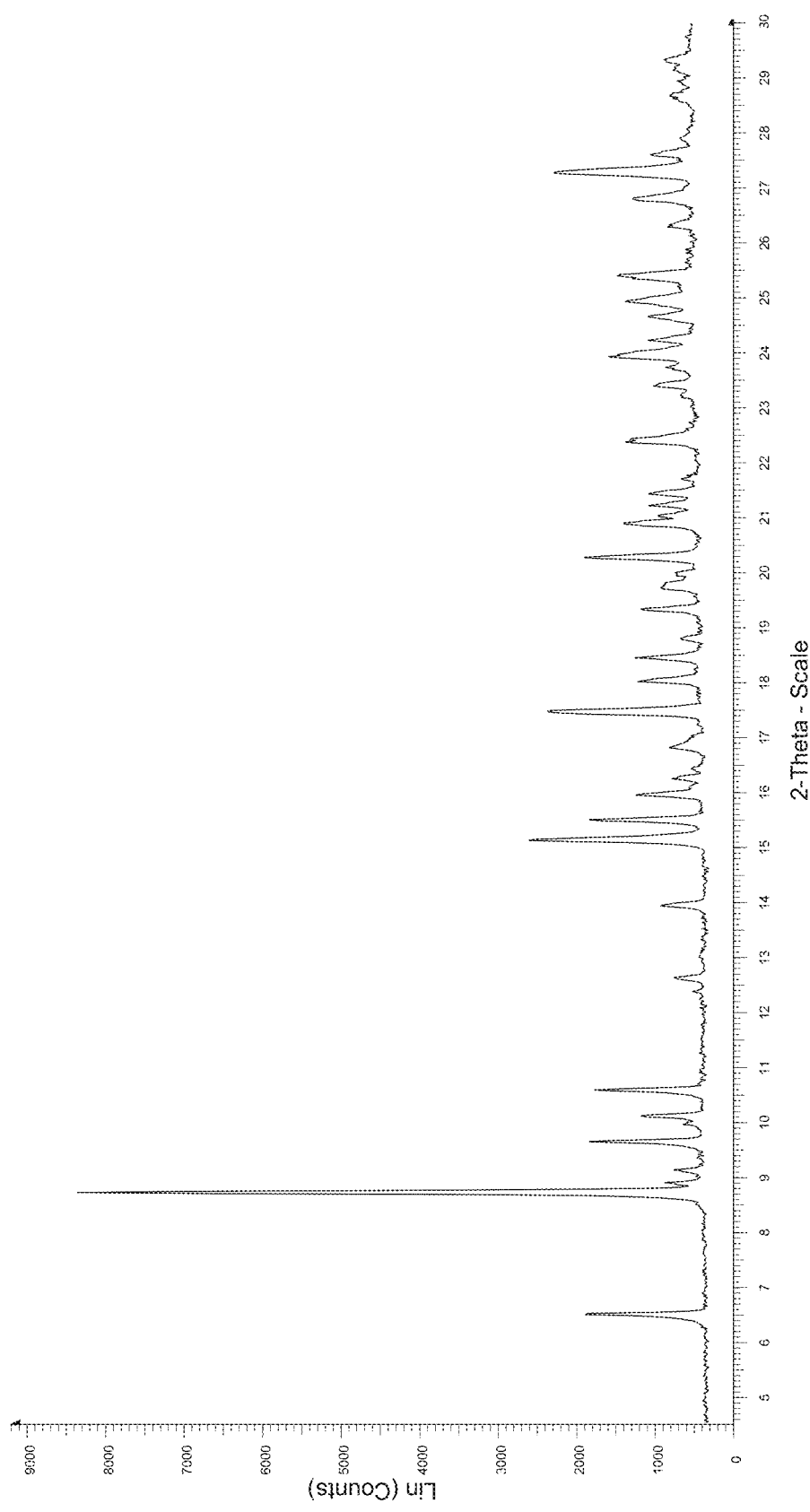
Figure 11:
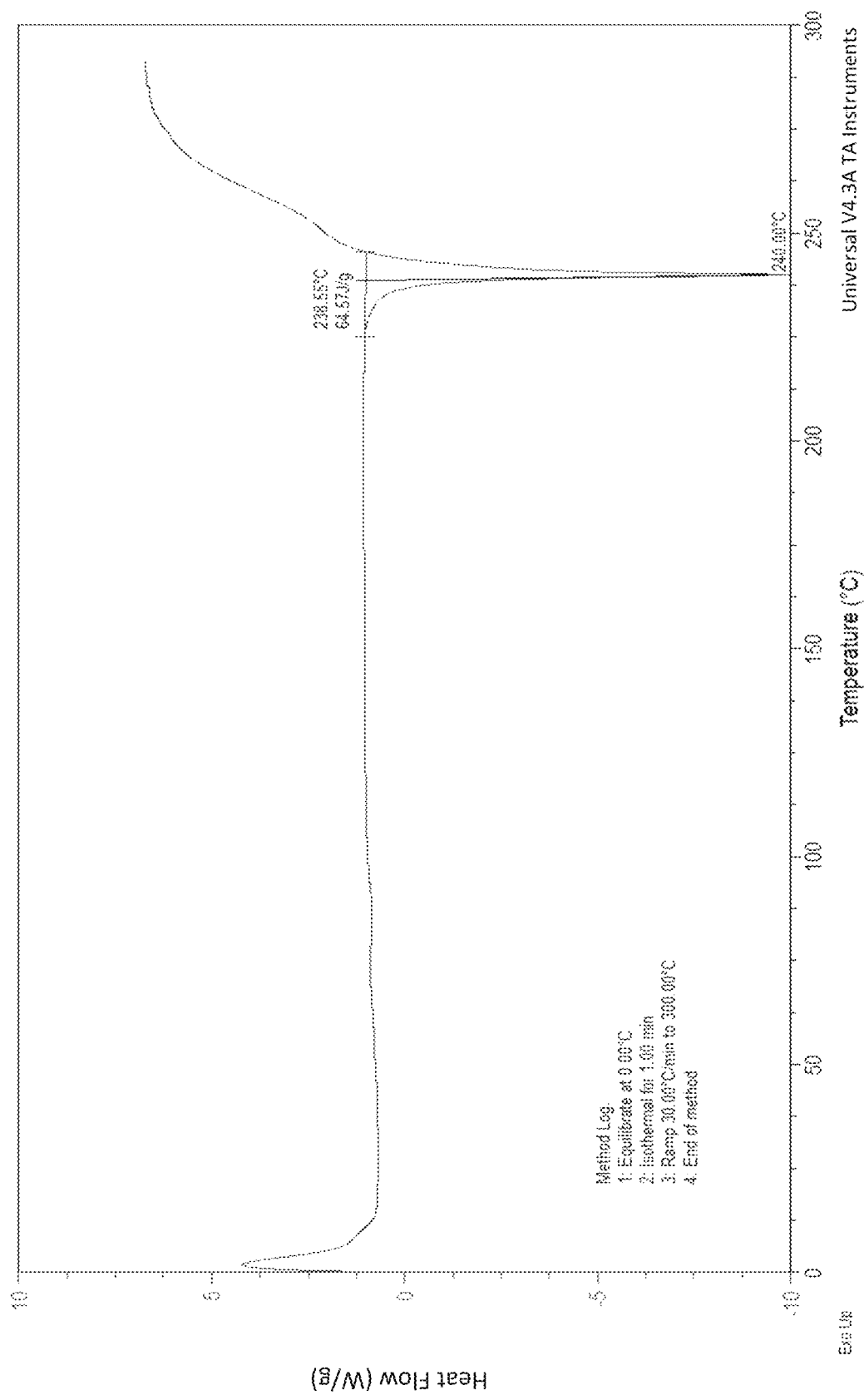
Figure 12:
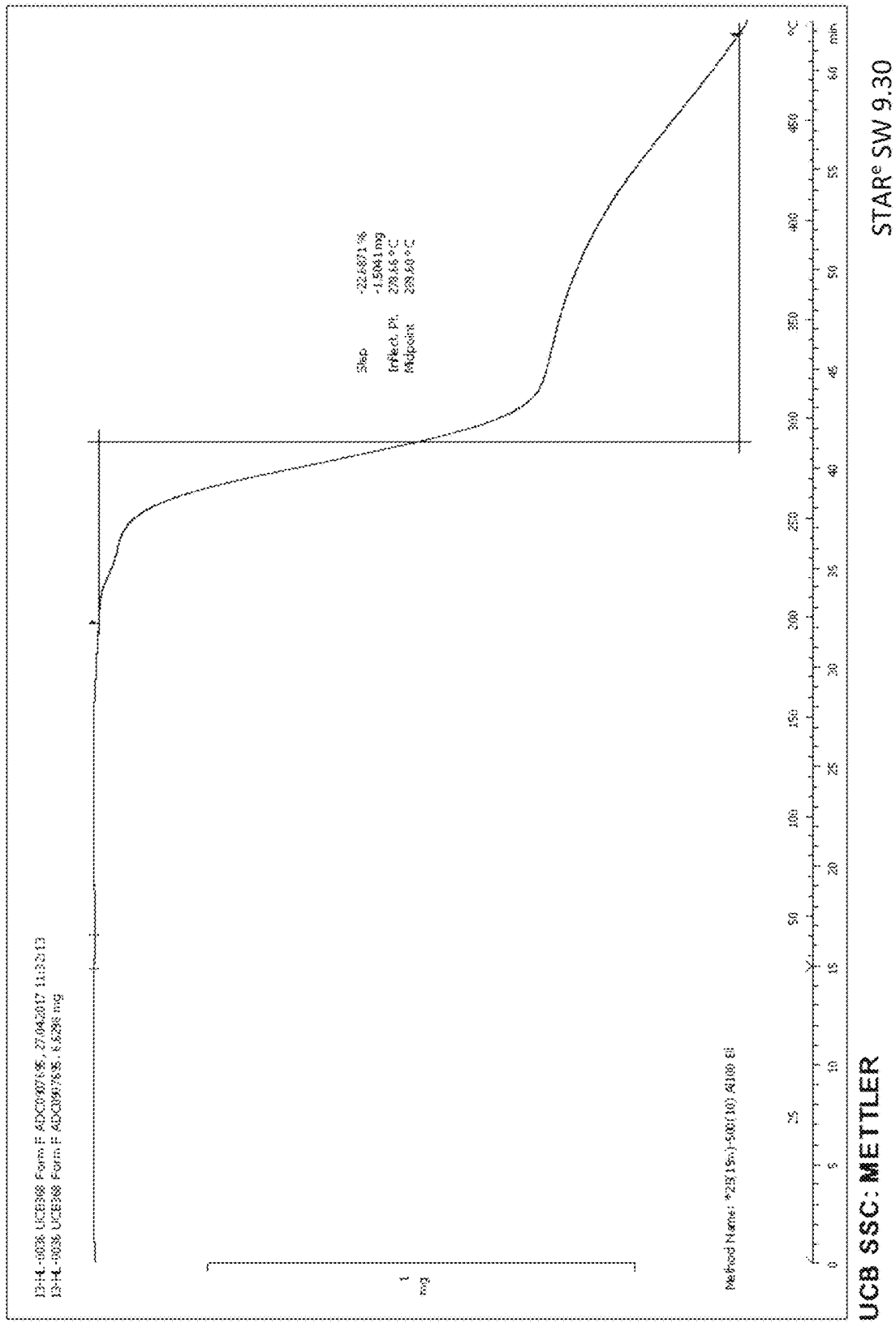
FIG. 12 shows the TGA thermogram of the anhydrous form. The shallow continuous slope at the start represents some solvent at the surface of the crystals, whilst the true weight loss starting from 210° C. corresponds to the melting and decomposition.
Figure 13:
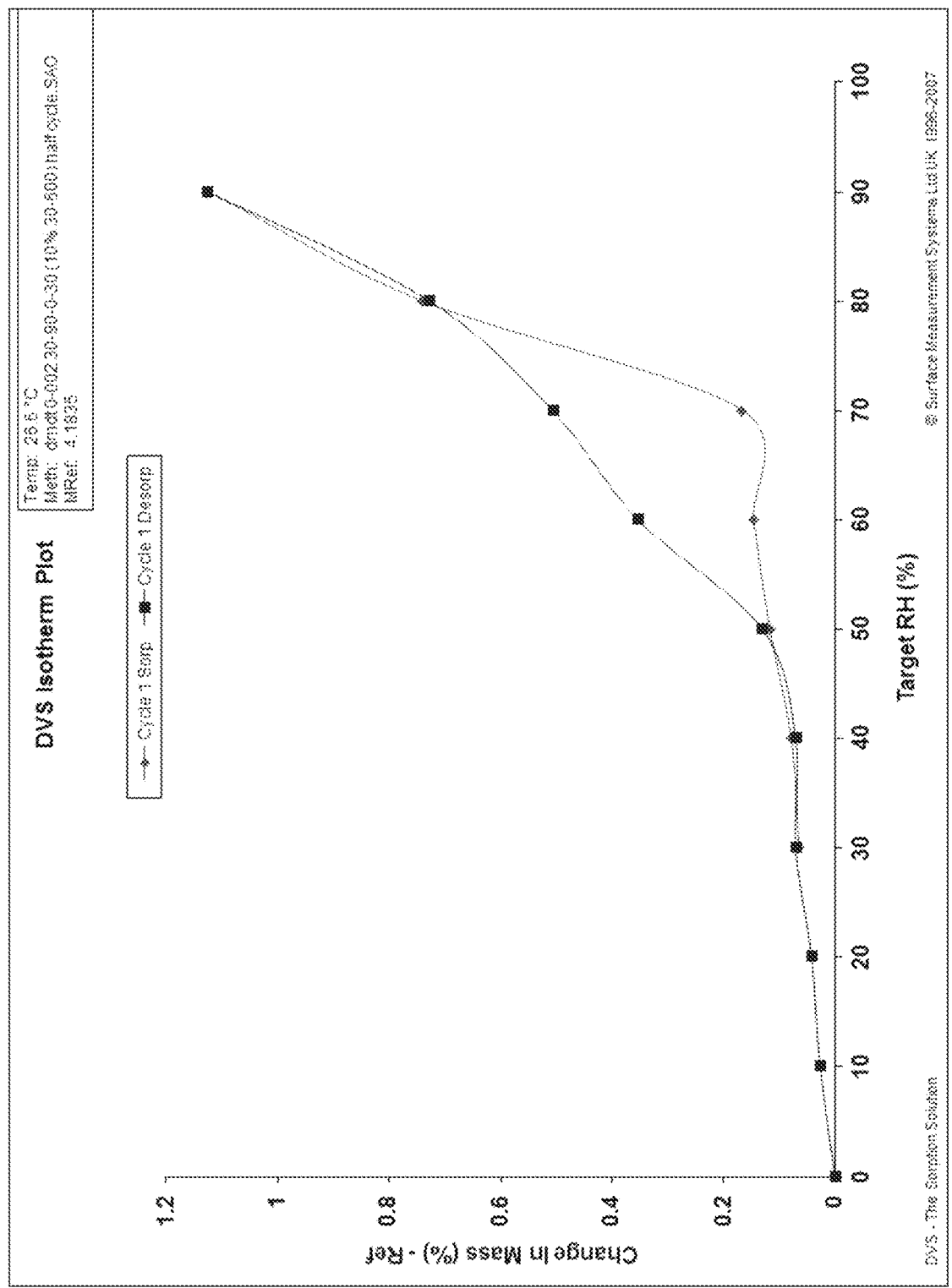
FIG. 13 depicts the DVS curve, showing the water sorption and desorption of the anhydrous form under variable relative humidity. The diagram shows the non-hygroscopic behaviour of the anhydrous form with a limited water uptake of 1% observed from 70% RH onwards.
Figure 14:
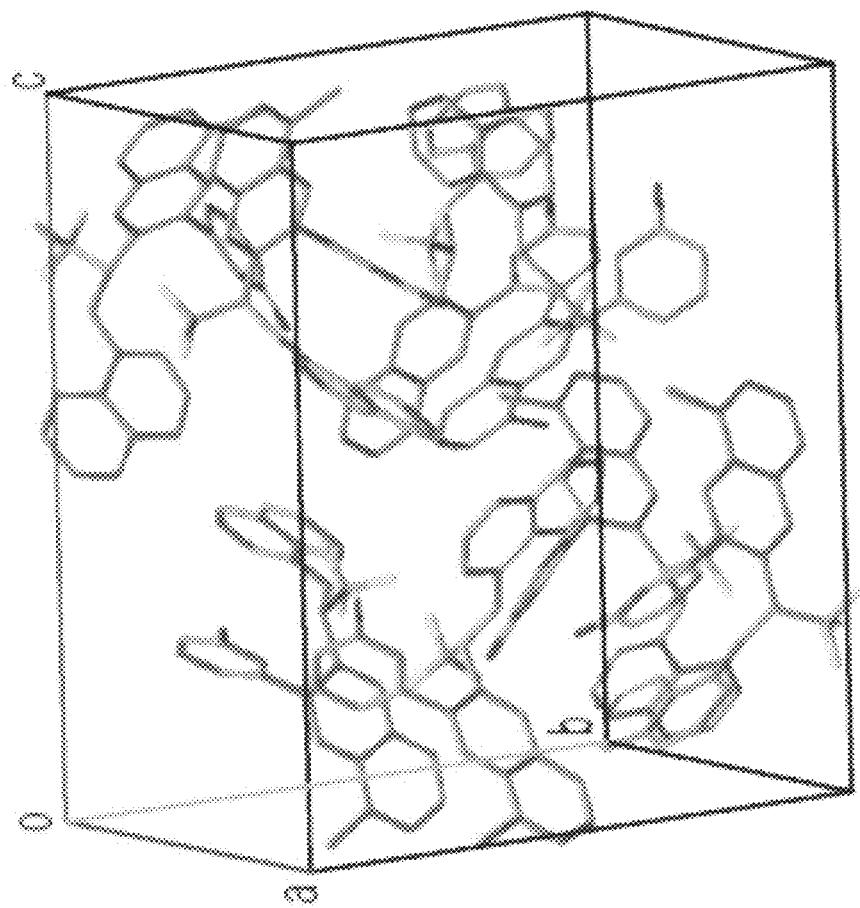

FIG. 14 illustrates the crystal packing of the anhydrous form.

Thermodynamic and Kinetic Stability of Form F

The anhydrous solid form (Form F) was found not to be thermodynamically stable under ICH conditions, meaning 25° C./60% RH and 40° C./75% RH. The thermodynamic stability was checked by suspending crystals of Form F for 30 days in appropriate solvent/water mixtures, as explained above for Form B crystals. The anhydrous solid form was nevertheless found to be kinetically stable under ICH conditions, which means exposing solid, powdery samples to air at selected temperature and relative humidity. Thus, Form F was found to be kinetically stable for 7 weeks at 25° C./60% RH and at 40° C./75% RH.

The invention claimed is:

1. Form B of seletalisib, wherein Form B is a hydrated crystal form thereof, represented by formula (IA):

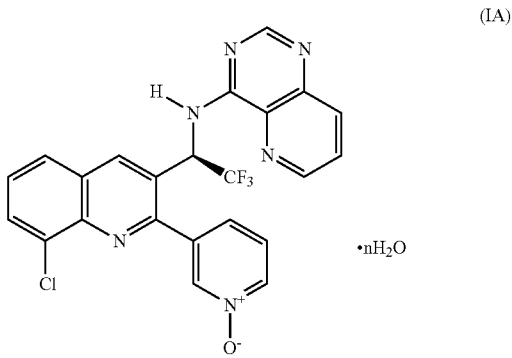 [SMILES: [O-][n+]1cccc(-c2nc3c(Cl)cccc3cc2[C@@H](Nc2ncnc3cccnc23)C(F)(F)F)c1]

(IA)

wherein n is at least 0.9 and no more than 2.1, having an XRPD pattern that exhibits characteristic peaks at 11.0° to 11.1°, 12.5° to 12.6°, 20.9° to 21.1°, and 22.9° to 23.0° 2θ±0.2° 2θ using Cu Kα radiation.

2. Form B of seletalisib as claimed in claim 1, wherein n is 1.0.

3. Form B of seletalisib as claimed in claim 1, wherein n is 2.0.

4. Form B of seletalisib as claimed in claim 1, that exhibits an endothermic event at 146° C.±6° C. in a DSC thermogram.

5. Form F of seletalisib, wherein Form F is an anhydrous crystal form thereof, having an XRPD pattern that exhibits characteristic peaks at 6.4°, 8.7°, 15.2°, 15.5°, and 20.3° 2θ±0.2° 2θ using Cu Kα radiation.

6. Form F of seletalisib as claimed in claim 5, that exhibits a melting endotherm at 238.5° C.±5° C. in a DSC thermogram.

7. A process for the preparation of Form F of seletalisib, which comprises reacting the compound of formula (II) with a compound of formula (III):

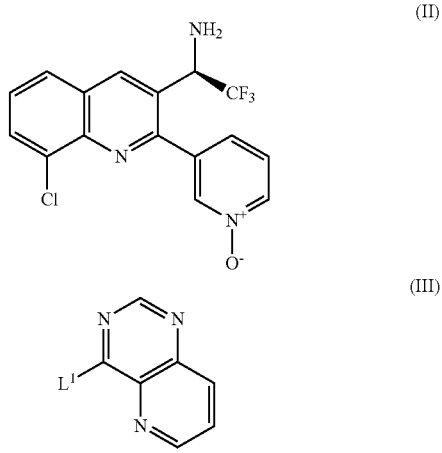

wherein $L^1$ represents $C_{1-6}$ alkoxy, optionally substituted aryloxy, optionally substituted arylthio or optionally substituted heteroaryl; in the presence of an acid, at an elevated temperature in an anhydrous solvent.

8. A process as claimed in claim 7, wherein $L^1$ represents methoxy, ethoxy, n-propoxy, n-butoxy, isobutoxy, phenoxy, pentafluorophenoxy, 4-chlorophenoxy, 4-nitro-phenoxy, 4-methylphenoxy, 2,4,6-trimethylphenoxy, 4-methoxyphenoxy, phenylthio, imidazol-1-yl, 1,2,4-triazol-1-yl or 4-(dimethylamino)pyridinium-1-yl.

9. A process as claimed in claim 8, wherein $L^1$ represents ethoxy.

10. A process for the preparation of Form B of seletalisib, which comprises contacting Form F of seletalisib with water in an organic solvent; followed by crystallization therefrom.

11. A process for the preparation of Form F of seletalisib, which comprises contacting Form B of seletalisib with a water-free medium; followed by crystallization therefrom.

12. A pharmaceutical composition comprising Form B of seletalisib as defined in claim 1 in association with a pharmaceutically acceptable carrier.

13. A pharmaceutical composition comprising Form F of seletalisib as defined in claim 5 in association with a pharmaceutically acceptable carrier.

* * * * *